(12) United States Patent
Yamazaki et al.

(10) Patent No.: US 7,329,252 B1
(45) Date of Patent: Feb. 12, 2008

(54) APPARATUS FOR LASER DEPILATION

(75) Inventors: Iwao Yamazaki, Tokyo (JP); Yoshihiro Izawa, Tokyo (JP)

(73) Assignee: Ya-Man Ltd., Koto-ku, Tokyo (JP)

( * ) Notice: Subject to any disclaimer, the term of this patent is extended or adjusted under 35 U.S.C. 154(b) by 0 days.

(21) Appl. No.: 10/275,966

(22) PCT Filed: May 19, 2000

(86) PCT No.: PCT/JP00/03225

§ 371 (c)(1),
(2), (4) Date: Nov. 18, 2002

(87) PCT Pub. No.: WO01/87109

PCT Pub. Date: Nov. 22, 2001

(51) Int. Cl.
*A61B 18/20* (2006.01)
*A61N 5/067* (2006.01)

(52) U.S. Cl. ............... 606/9; 606/3; 606/10; 607/88
(58) Field of Classification Search .......... 606/3, 606/9–13, 16–19; 607/88, 89
See application file for complete search history.

(56) References Cited

U.S. PATENT DOCUMENTS

| | | | | |
|---|---|---|---|---|
| 4,388,924 A | * | 6/1983 | Weissman et al. | 606/9 |
| 5,658,323 A | * | 8/1997 | Miller | 607/89 |
| 5,735,844 A | * | 4/1998 | Anderson et al. | 606/9 |
| 6,149,644 A | * | 11/2000 | Xie | 606/9 |
| 6,273,883 B1 | * | 8/2001 | Furumoto | 606/9 |
| 6,383,176 B1 | * | 5/2002 | Connors et al. | 606/9 |
| 6,572,637 B1 | * | 6/2003 | Yamazaki et al. | 607/89 |
| 6,790,205 B1 | * | 9/2004 | Yamazaki et al. | 606/9 |
| 7,214,222 B2 | * | 5/2007 | Yamazaki et al. | 606/9 |

* cited by examiner

*Primary Examiner*—A. Farah
(74) *Attorney, Agent, or Firm*—Bacon & Thomas, PLLC

(57) ABSTRACT

An apparatus for laser depilation according to the present invention uses a semiconductor laser diode, which is controlled in respect of its energy level, thereby permitting an economical, effective and safe cosmetic treatment. The power output of light of the semiconductor laser diode ranges from 5 to 1500 mW, and the peak wavelength ranges from 600 to 1600 nm. The controller of the semiconductor laser diode comprises pulsating power output control means and radiation period control means for setting a desired length of time for radiation. With these control means the energy level of the beam of light from the laser may be so controlled that a strong beam of light may be thrown for a relatively short time, or that a weak beam of light may be thrown for a relatively long time. Thus, hairs of different thickness and colors can be removed.

1 Claim, 7 Drawing Sheets

APPARATUS FOR LASER DEPILATION

TECHNICAL FIELD

The present invention relates to a cosmetic apparatus for laser depilation using a semiconductor laser diode in effecting a required depilation treatment.

BACKGROUND ART

One factor for growing hairs is a certain kind of protein called "Keratin", which is supplied from hair papillae and sebum vessels in the pores of the skin.

Laser depilation is effected by throwing a laser beam onto a selected spot on the skin, thereby causing denaturation of protein to prevent the supply of Keratin with the result that hair growth is prevented.

When the intense beam of light is thrown from the laser onto a selected area of the skin, a Joule heat will be generated to cause a variety of opto-thermo reactions, depending on the raised temperature of the organism at the selected area, as for instance the following may occur: carbonization is caused at 400 or higher degrees C.; vaporization at 100 or higher degrees C.; blood coagulation at 68 or higher degrees C.; and activation at 40 or lower degrees C.

A temperature rise of the organism above 42 degrees C. will cause denaturation of protein, thereby causing cells to die. If the number of dead cells should increase beyond a certain limit, the organism cannot return to its original state.

In effecting a required depilation treatment safely and effectively, therefore, it is necessary that the strength of the laser beam is so controlled that the temperature of the organism may not rise significantly above 42 degrees C.

A laser device for medical use can produce a laser beam of light strong enough to effect a required depilation efficiently. Common people other than authorized medical experts are not permitted to use such a laser device for medical operations, which is very expensive, also.

For these reasons the medical treatment of depilation by using a medical laser is expensive, and still disadvantageously the depilation treatment is restricted by time.

Also, people are liable to feel less pleasing to the medical depilation, desiring that a required depilation be effected like an aesthetic treatment.

In the hope of meeting such a demand one object of the present invention is to provide a cosmetic apparatus for depilation using a semiconductor laser diode, which is capable of producing a beam of light at a controlled energy level, different from an intense beam of light produced by the medical laser, thereby permitting common people to handle the semiconductor laser diode in effecting a required depilation economically and safely.

SUMMARY OF THE INVENTION

Apparatus for laser depilation according to the present invention is constructed as follows:

use is made of a semiconductor diode whose light power output ranges from 5 to 1500 mW, the peak wavelength ranging from 600 to 1600 nm. A condenser lens is put ahead of the semiconductor laser diode.

Light power output control means and radiation period control means are provided to control the beam of light from the laser in respect of energy level.

The light power output control means controls the light power output of the laser beam in respect of the length of pulse-on time, whereas the radiation period control means sets the length of radiation period within the range of 1 to 9 seconds, the length of radiation period thus set alternating with a given length of dormacy period.

With the aid of the light power output control means and of the radiation period control means the energy level of the laser beam to be thrown onto the skin is controlled to be appropriate for causing denaturation of protein in the hair papillae and sebum vessels to prevent the growth of hairs.

DESCRIPTION OF THE PREFERRED EMBODIMENTS

Figure 1:
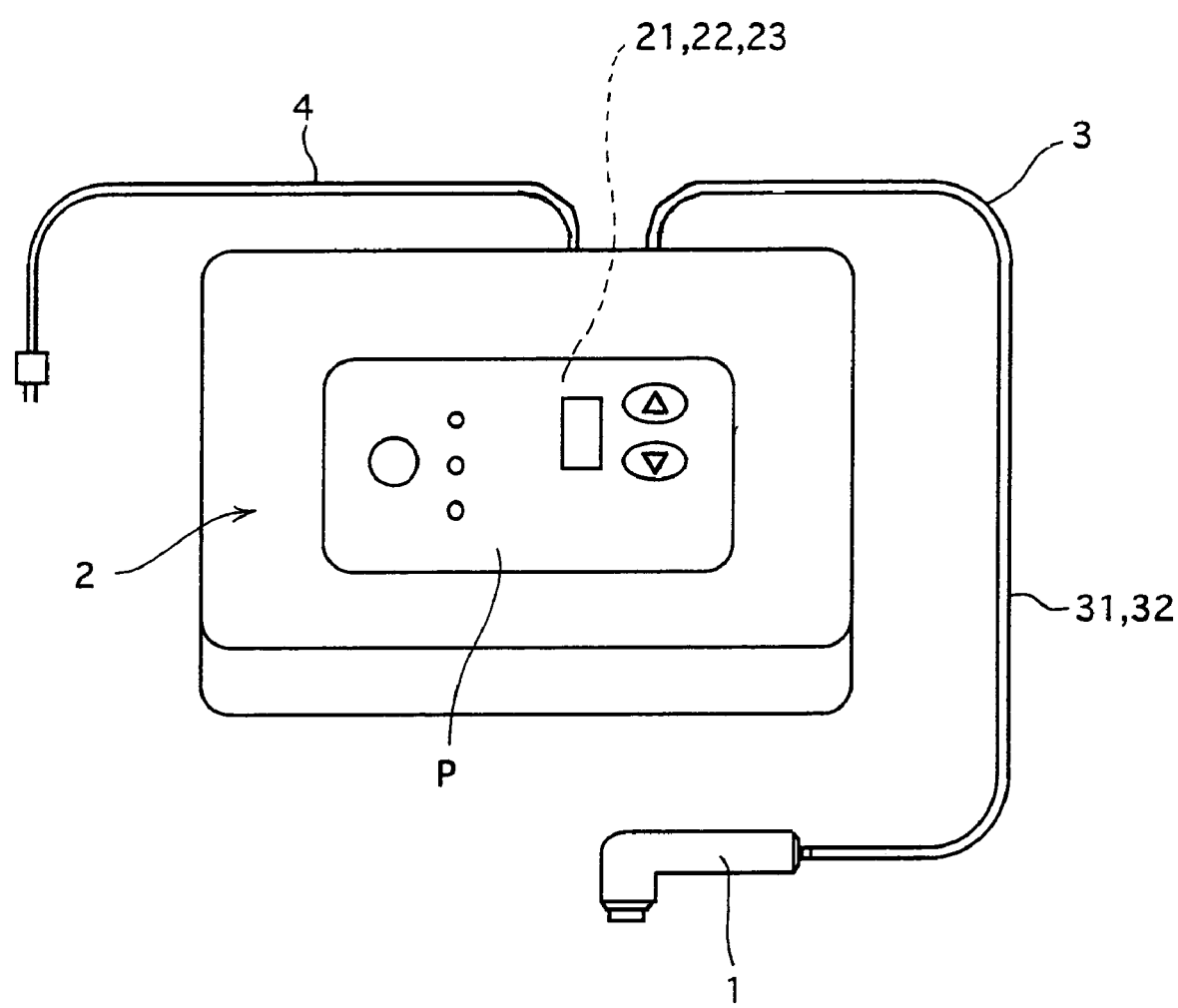
FIG. 1 shows the whole structure of an apparatus for laser beam depilation according to the present invention.
Figure 2:
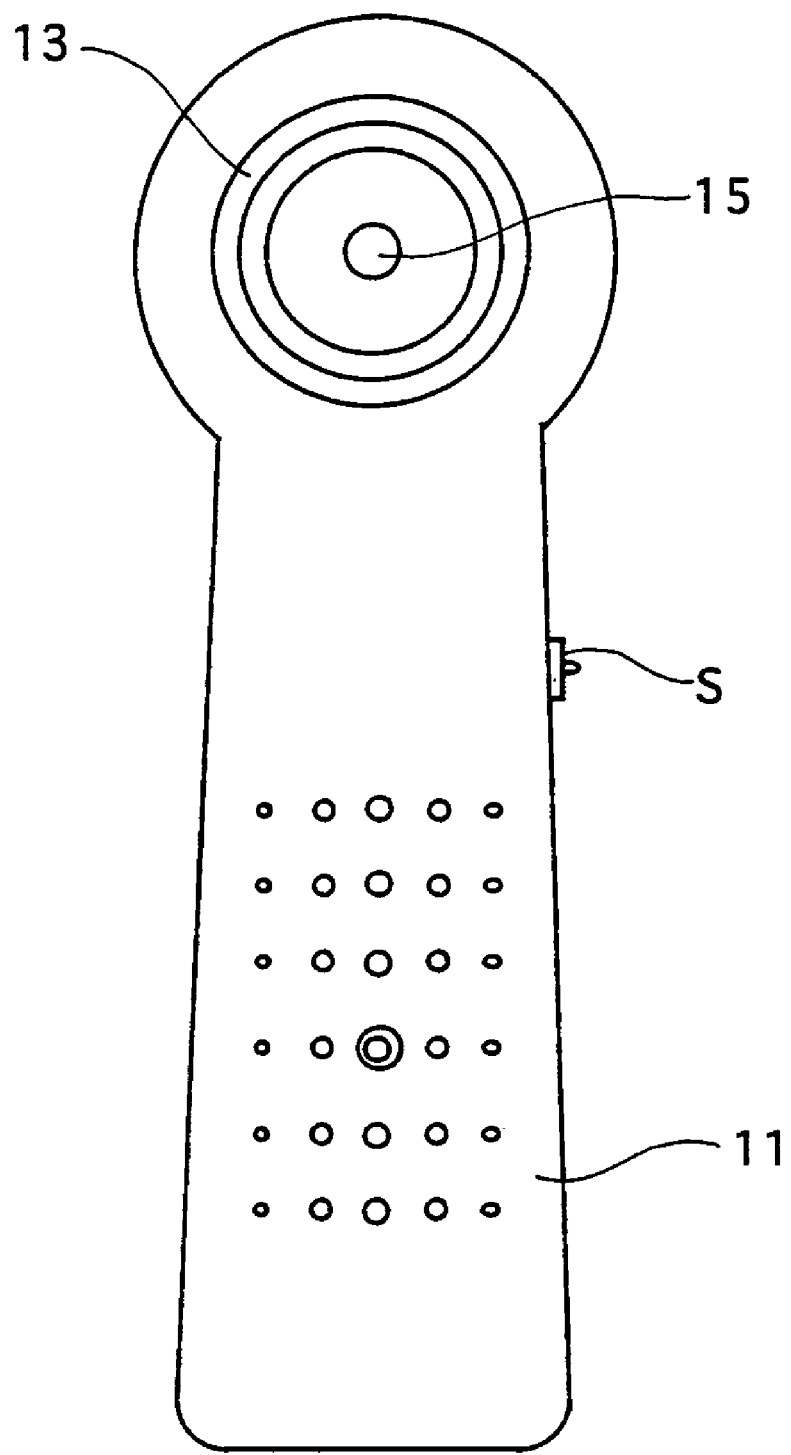
FIG. 2 is an enlarged front view of a laser beam projector of the apparatus for laser beam depilation of FIG. 1.
Figure 3:
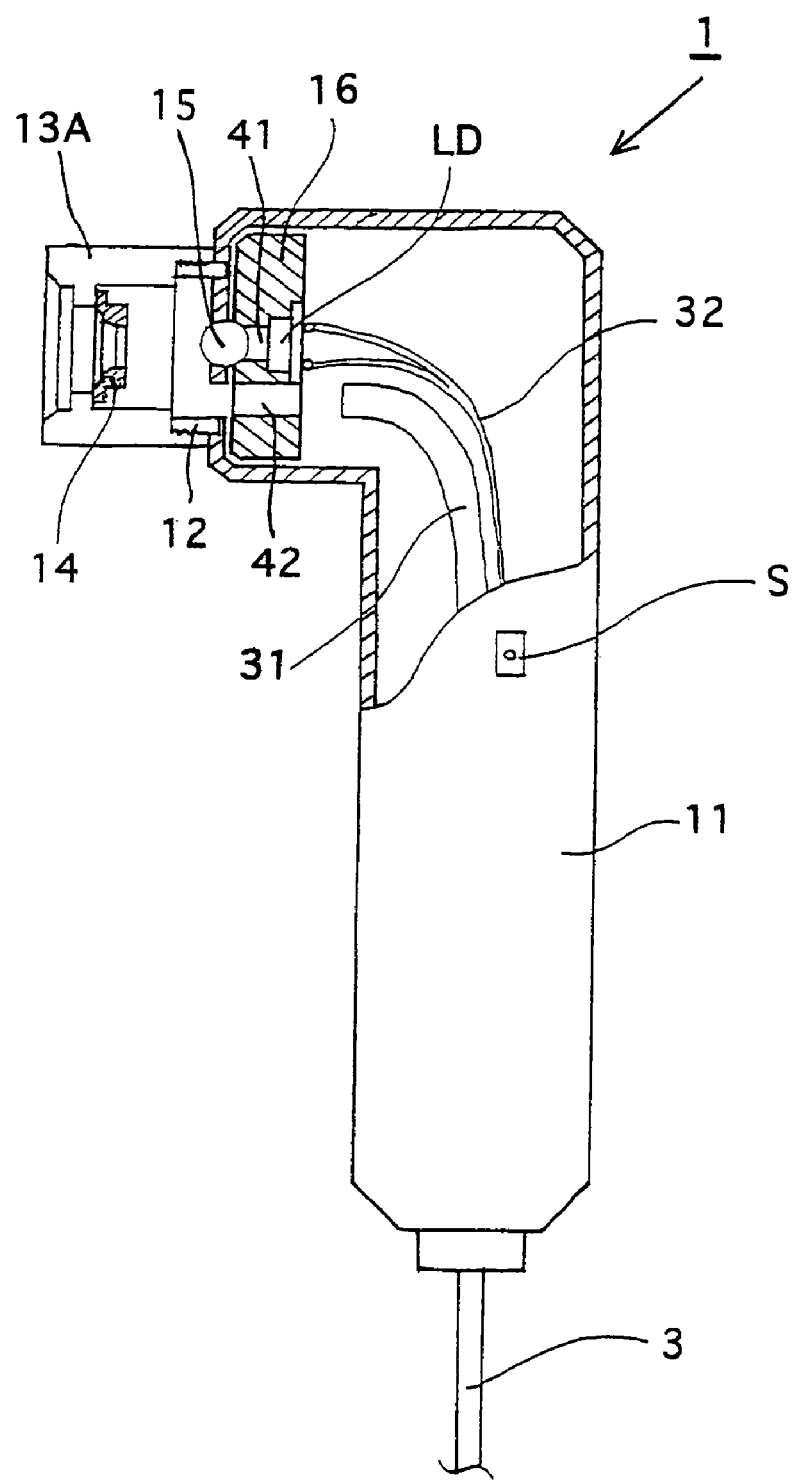
FIG. 3 is a side view of the laser beam projector, partly in section.

Referring to the drawings, an apparatus for laser beam depilation comprises a laser projector 1 and a control unit 2

The control unit 2 has a console P on its front side and electric cables 3 and electric cord 4 on its rear side for connecting the control unit 2 to the outlet, and the control unit 2 has a compressor 21 for sucking and ejecting air, a power supply 22 for a laser diode, and a control circuit 23 for controlling the sucking and ejecting of air in respect of time and for controlling the turning on-and-off of the laser diode LD in respect of time, which laser diode LD is installed in the laser projector 1.

The turning on-and-off of the power supply switch, the pulsating power output, the radiation period, the whole period set for effecting a required treatment, selection of a desired treatment mode and other factors can be determined by using the console P.

The pulsating power output can be controlled by controlling the electric power supply 22 for the laser diode LD. Specifically the beam of light can be pulsated by making the power supply 22 turn on and off, and the energy of the beam of light can be controlled in terms of duty ratio.

When the user desires to increase the energy of the beam of light, the length of period for which the power supply 22 is made to turn on is extended, and accordingly the length of time for spot illumination is extended per unit time. When the user desires to decrease the energy of the beam of light, the length of period for which the power supply 22 is made to turn on is shortened, and hence the length of time for spot illumination is shortened per unit time. The energy output can be maximized by making the electric power supply turn on continuously. Pulse recurrence ranges from 5 to 100 Hz.

As may be understood from the above, the beam of light from the laser diode LD is pulsated or is made to continue. As for the pulsating of the beam of light a series of pulses are chopped at regular intervals, as for instance, follows: if the continuous duration of pulsating power output or radiation period is set at 5 seconds, the laser diode LD turn on 5 seconds, and then, it remains dormant for 3 seconds. The sequence of operation-and-dormancy is repeated. Appearance of dormancy at regular intervals is effective to avoid the danger of damaging the skin by a single elongated shot. The radiation period can be controlled in the range from 1 to 9 seconds.

Pulsating energy output and radiation period are controlled, depending on the color and thickness of hairs. For example, when it is desired that black, thick hairs are removed, the duty ratio of pulsating energy is increased to increase the pulsating energy output while shortening the radiation period. Thus, the controlled intense beam of light is thrown onto a selected spot on the skin to suppress the growth of hairs without hurting the skin. When golden, fine hairs are removed, the duty ratio of pulsating energy is decreased to decrease the pulsating energy output while lengthening the radiation period. Thus, hairs can be removed without hurting the skin. In either case the amount of energy is almost equal, but the biological effect on the organism is different. Thus, the spot illumination of laser beam is controlled to be most appropriate for the purpose in respect of the kind of hairs.

The required treatment is effected by repeating the sequence of operation-and-dormancy of the laser. To prevent any damage from causing on the skin the total length of time is selected by setting the timer on the apparatus in the range from 5 to 60 minutes.

A desired operation mode can be selected among "exclusive laser operation", "laser operation and air sucking", and "laser operation and air blowing".

The electric cord 3 contains an air tube 31 and electric wires 32. The air tube 31 connects the laser beam projector 1 to the compressor 21 whereas the electric wires 32 connect the laser beam projector 1 to the electric power supply 22 and the control circuit 23.

The laser beam projector 1 takes an L-shape, and its casing 11 has a switch S provided on one side, and a threaded ring 12 fastened to its head front.

Figure 4:
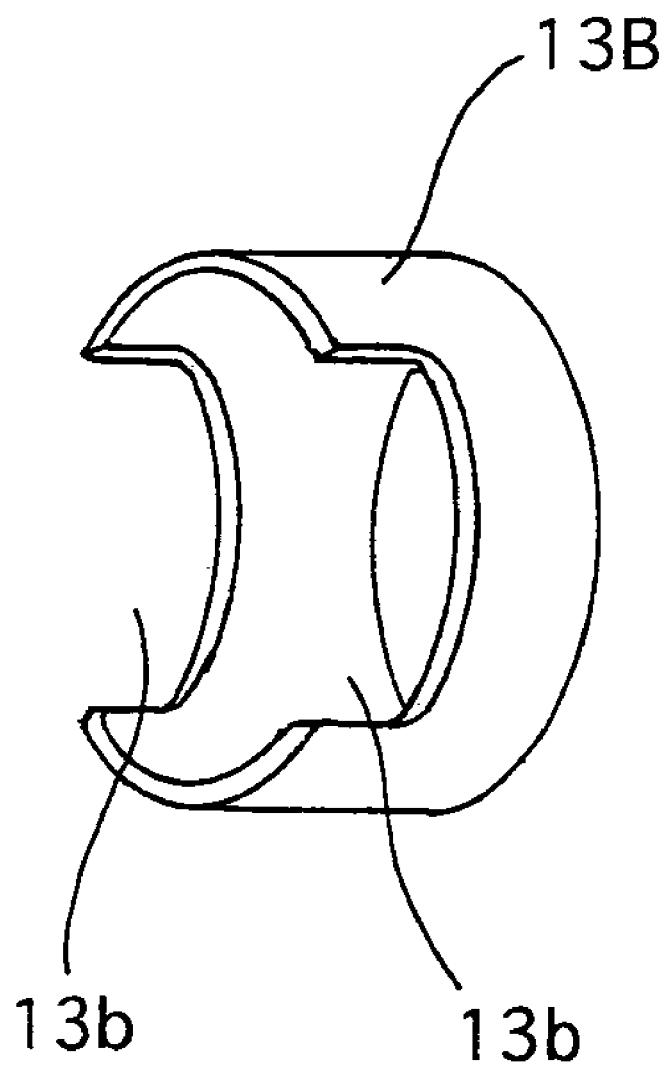
FIG. 4 is a perspective view of a blowing cap used in the laser beam projector.

An air-sucking cap 13A or an air blowing cap 13B (FIG. 4) can be detachably attached to the threaded ring 12 by screwing either cap around the male threads formed on the outer surface of the ring 12.

The air-sucking cap 13A or air-blowing cap 13B is made of transparent acrylic resin, thereby permitting one to realize which area of the skin is exposed to the beam of light.

The sucking cap 13A has an annular skin-toucher 14 of ABS resin attached inside.

The air-blowing cap 13B has vents 13b made on its annular side.

The casing 11 has a spherical condenser lens 15 placed in its head.

The coherent, directional beam of light from the laser is converged toward the focal point of the lens 15.

The air-sucking cap 13A or air-blowing cap 13B functions as a spacer to adjust the distance from the skin to the lens 15, which distance can be controlled by screwing the cap 13A or 13B around the threaded ring 12, thereby controlling the energy density of the beam of light from the laser.

A heat sink 16 is fastened to the inner surface of the head of the casing 11.

The heat sink 16 has a through hole 41 and a vent hole 42 made therein. The through hole 41 is made at the center of the heat sink 16 to allow the beam of light to pass therethrough, and the laser diode LD is placed behind the through hole 41.

The beam of light from the laser diode LD converges toward the axial center line of the opening of the skin-toucher 14 or air-blowing cap 13B.

The laser diode LD is a PN junction diode comprising a chemical semi-conductor such as GaAs, and the laser oscillation can be caused by making an electric current flow for stimulation.

The semiconductor laser diode is small and light, and it can produce a beam of light at an increased efficiency, permitting the beam of light to be modulated with electric current as required. The device is long lived, and less expensive.

The wavelength of the beam of light depends on the mixture ratio and kinds of materials used.

The wavelength of the beam of light is selected to be appropriate for depilation in respect of the color of the skin; the influence of the beam of light on the skin varies with the color of the skin.

A semiconductor laser diode produces a beam of light, of which: the peak wavelength ranges from 600 to 1600 nm and the light power output ranges from 5 to 1500 mW. Within such ranges the beam of light can cause a required photo-thermo reaction efficiently without the fear of hurting the organism at all.

The beam of light from the laser will cause a variety of effects other than the thermal effect useful for depilation, as for example follows: the photo-electric effect, photo-magnetic effect, photo-dynamic effect, photo-chemical effect, photo-immunification effect and photo-zimogic effect. These effects expedite the metabolism, thereby increasing the circulation of the blood in the skin. The laser beam is hardly absorbed in water and blood, and accordingly it can travel deep in the skin.

In a case that a single laser cannot produce a beam of light strong enough to remove hairs from the skin, lasers as many as required for depilation can be so arranged that their beams of light may converge toward a single spot.

The heat sink 16 can dissipate the heat generated in the laser diode LD by thermal conduction, thereby preventing the lowering of the light producing capability.

Also, vent holes are made in the heat sink to improve the heat radiation efficiency.

The air tube 31 extends from the compressor 21 to open behind the heat sink 16 in the casing 11.

The electric wires 32 extend from the electric supply 22 to the laser diode LD in the casing 11 of the laser beam projector 1.

Figure 5:
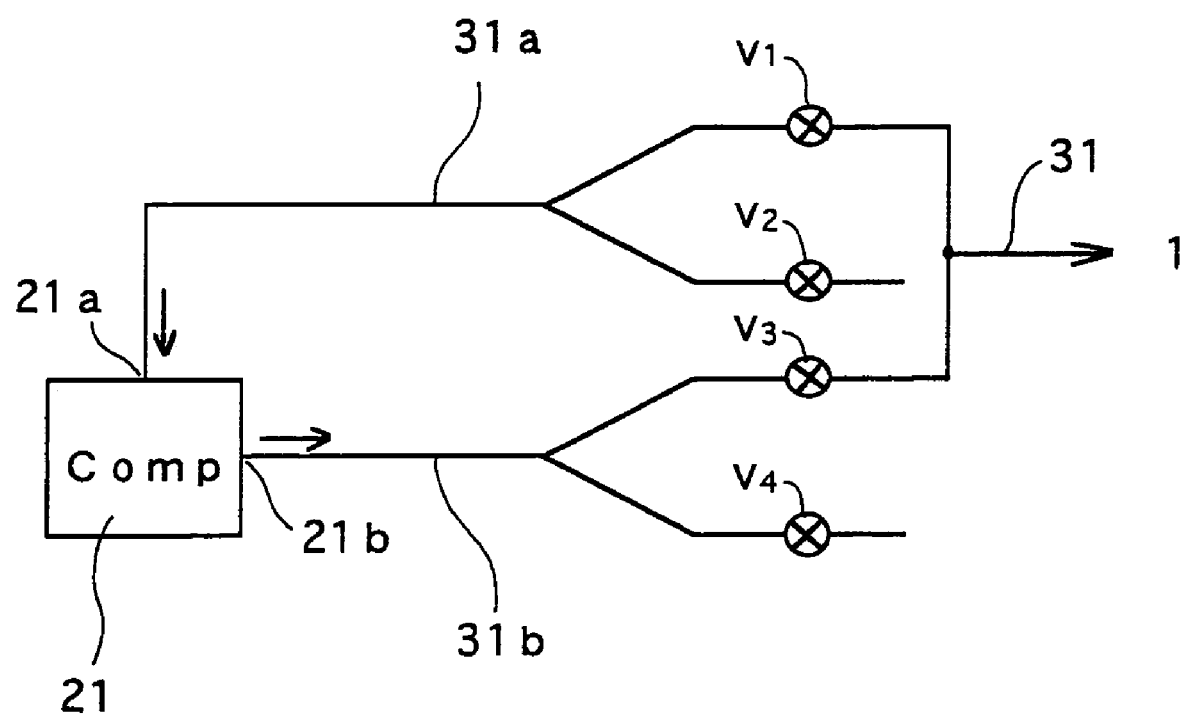
FIG. 5 shows the piping of a compressor of the apparatus for laser beam depilation of FIG. 1.

FIG. 5 shows the piping of the compressor 21.

As shown, the suction port 21a of the compressor 21 is connected to a first tube 31a, two branch tubes of which are connected to valves V1 and V2. Likewise, the ejection port 21b of the compressor 21 is connected to a second tube 31b, two branch tubes of which are connected to valves V3 and V4. The valves V1 and V3 are connected whereas the valves V2 and V4 open to the atmosphere.

Figure 6:
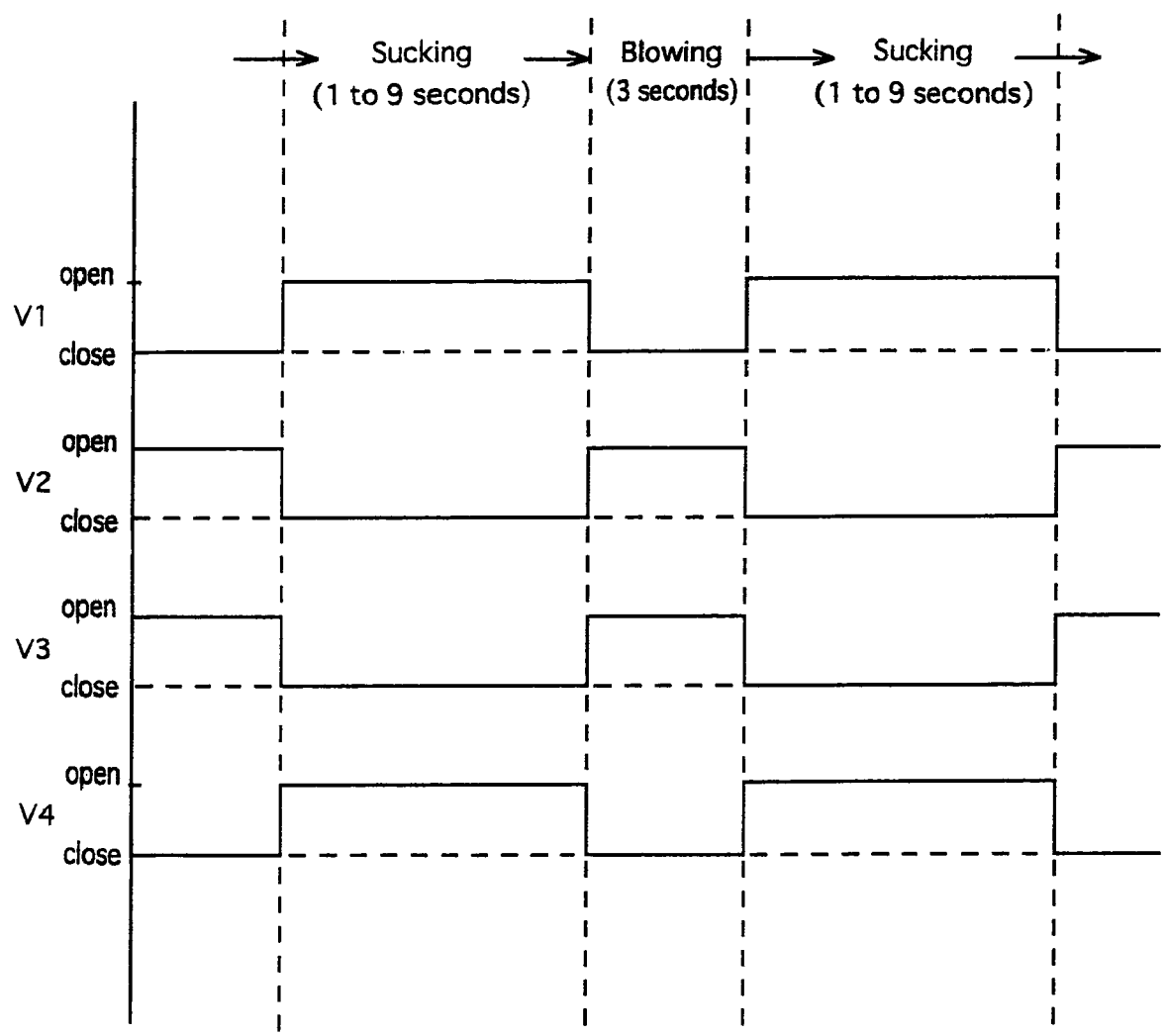
FIG. 6 is a time chart showing how the valves are operated.

Referring to FIG. 6, for sucking air into the laser beam projector 1 the valves V1 and V4 are opened, and the valves V2 and V3 are closed.

Conversely for blowing air from the laser beam projector 1 the valves V1 and V4 are closed, and the valves V2 and V3 are opened.

A simple type of laser beam projector 1 can blow, but cannot suck air into the laser beam projector 1. A valve-less tube is used in place of the tube 31a, and one branch tube of the tube 31b is connected to the air tube 31 via the valve V3, and the other branch tube is open to the surrounding via the valve V4.

Another simple type of laser beam projector 1 can suck, but cannot blow air from the laser beam projector 1. A valve-less tube is used in place of the tube 31b, and one branch tube of the tube 31a is connected to the air tube 31 via the valve V1, and the other branch tube is open to the surrounding via the valve V2.

A required laser treatment is effected 5 to 60 minutes while alternating radiation and dormancy with each other.

One shot is set at 1 to 9 seconds, and the inter-shot dormancy is set at 3 seconds. Air is made to blow during the dormancy.

The blowing of air during dormancy improves the cooling effect in the laser beam projector 1.

When the sucking or blowing is required in the treatment mode, radiation of the laser beam is effected in parallel with the sucking or blowing of air.

The apparatus for laser beam depilation constructed as such can be operated as follows: first, the optical power output, the radiation period, the period for treatment, the operation mode and such like are determined and set on the console P.

Depilation cream is applied to a selected spot on the skin, so that the hairs are melted and removed there.

When the sucking is desired, the suction cap 13A is attached to the head of the laser beam projector 1. The suction cap 13A is screwed around the head ring 12 to adjust the skin-toucher 14 in position.

Then, the laser beam projector 1 is applied to the selected spot on the skin, and the push switch button S is depressed.

Thus, the skin surface is drawn and applied to the skin-toucher 14, where the beam of light is thrown from the laser.

The skin spot is exposed for example, 5 seconds (radiation period), and the spot illumination is made to cease about 3 seconds. Air blows from the head of the laser beam projector 1 the while.

Then, the skin surface leaves the skin-toucher 14, and the laser beam projector 1 is moved to the next spot for treatment.

The above described process is repeated for the treatment period.

When the blowing is required, a blowing cap 13B is attached to the head ring 12 by screwing it around the head ring 12 while adjusting the notchs of the blowing cap 13B in position.

After applying the head of the laser beam projector 1 onto the skin the push switch button S is depressed.

Then, air blows from the head of the laser beam projector 1, and the beam of light is thrown onto the skin.

A three minute-long dormancy follows, still allowing air to blow the while.

The process is repeated for the period of treatment.

As the air is blowing, the skin spot exposed to the beam of light is cooled, thereby suppressing the excessive rise of temperature at the skin spot. A good photo-thermo effect is caused in the skin.

Figure 7:
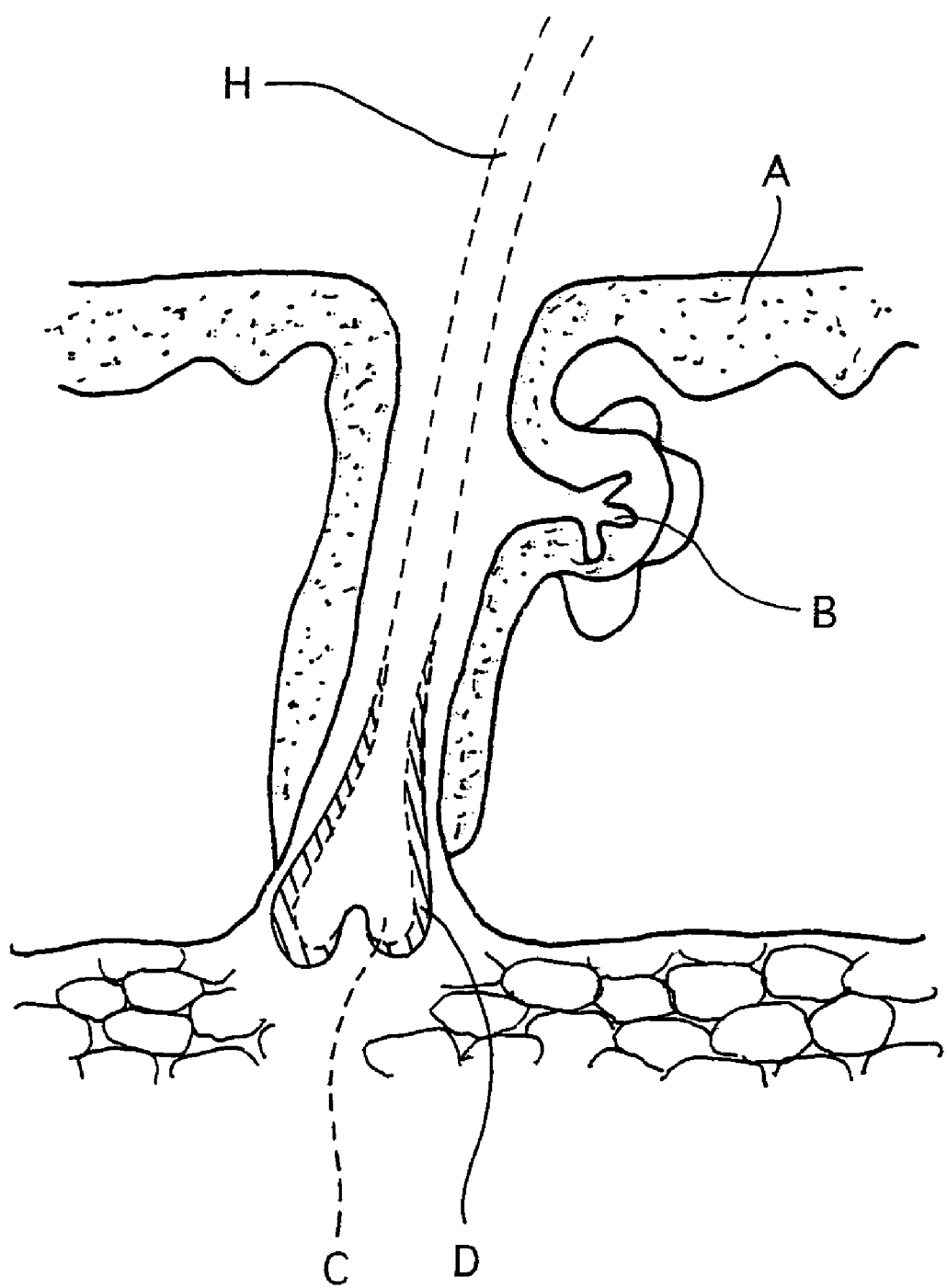
FIG. 7 illustrates, in section, the structure of skin to be exposed to the laser beam.

Referring to FIG. 7, depilatory cream is applied to a selected area of the skin to remove hairs H, and then the area of the skin is exposed to the beam of light from the laser. The beam of light is absorbed by melanin A in the epiderm, so that heat is produced to shrink the sebum vessels B and hair papillae C. As a result the pore is reduced in size.

The sebum vessels B and hair papillae C are damaged, and therefore, the follicle organism D is so hardened that lanugs may grow hardly. Thus, the growth of hairs is suppressed.

INDUSTRIAL APPLICABILITY

As may be understood from the above, an apparatus for laser depilation according to the present invention uses a semiconductor laser diode whose power outputs of light range from 5 to 1500 mW with the peak wave length ranging from 600 to 1600 nm, and a condenser lens is put ahead of the semiconductor laser diode. The apparatus further comprises light power output control means for controlling the pulsating optical power output, and radiation period setting means.

The apparatus for laser depilation uses a semiconductor laser providing as low as to 1500 mW, and there is no fear of the skin being harmed. For this reason the depilation apparatus is most appropriate for use in depilation for cosmetic purpose; a safety is of great concern in the cosmetic treatment. The semiconductor laser diode used is less expensive than other types of lasers.

Semiconductor laser diodes of different wave lengths are available, and therefore, a selection can be made among those lasers in respect of the color of the skin.

The concentration, power output and radiation period of the beam of light from the laser can be so controlled that the level of the optical energy thus provided may be most appropriate for individual depilation treatments from the points of view of safety and efficiency.

The invention claimed is:

1. An apparatus for laser depilation, comprising:
a semiconductor laser diode of which the power output of light ranges from 5 to 1500 mW, and of which the peak wavelength ranges from 600 to 1600 nm;
a condenser lens downstream of said semiconductor laser diode;
light power output control means for controlling the light power output of the laser beam with respect to the length of pulse-on time; and
radiation period control means for setting a desired length of radiation period within the range of 1 to 9 seconds, the length of radiation period thus set alternating with a given length of dormancy period, whereby with the aid of the light power output control means and of the radiation period control means a most appropriate control may be effected in respect of energy level to expose a selected area of the skin to the controlled laser beam, thus causing denaturation of protein in the hair papillae and sebum vessels, thereby suppressing the growth of hairs;
a laser projector within which said semiconductor laser diode and said condenser lens are mounted; and
a heat sink mounted to said laser projector, wherein:
said semiconductor laser diode is mounted to said heat sink.

* * * * *